(12) United States Patent
Akiyama et al.

(10) Patent No.: US 11,357,605 B2
(45) Date of Patent: Jun. 14, 2022

(54) METHOD FOR MANUFACTURING CERAMIC SINTERED BODY

(71) Applicant: ADAMANT NAMIKI PRECISION JEWEL CO., LTD., Tokyo (JP)

(72) Inventors: Yusuke Akiyama, Kawaguchi (JP); Shinichi Takeda, Tokyo (JP); Kazuyuki Syoji, Yokote (JP); Hideyuki Kanno, Yokote (JP)

(73) Assignee: ADAMANT NAMIKI PRECISION JEWEL CO., LTD., Tokyo (JP)

( * ) Notice: Subject to any disclaimer, the term of this patent is extended or adjusted under 35 U.S.C. 154(b) by 0 days.

(21) Appl. No.: 16/479,460

(22) PCT Filed: Dec. 18, 2017

(86) PCT No.: PCT/JP2017/045334
§ 371 (c)(1),
(2) Date: Jul. 19, 2019

(87) PCT Pub. No.: WO2018/139105
PCT Pub. Date: Aug. 2, 2018

(65) Prior Publication Data
US 2019/0388197 A1 Dec. 26, 2019

(30) Foreign Application Priority Data
Jan. 27, 2017 (JP) .............................. JP2017-013207

(51) Int. Cl.
*A61C 13/00* (2006.01)
*A61C 13/08* (2006.01)
(Continued)

(52) U.S. Cl.
CPC ........ *A61C 13/0022* (2013.01); *A61C 13/082* (2013.01); *A61C 13/083* (2013.01);
(Continued)

(58) Field of Classification Search
CPC . A61C 13/0022; A61C 13/082; A61C 13/083; C04B 35/64; G01N 3/40; G01N 9/00; G01N 33/388
See application file for complete search history.

(56) References Cited

U.S. PATENT DOCUMENTS 6,066,584 A 5/2000 Krell et al.
7,604,759 B2 10/2009 Gubler et al.
(Continued)

FOREIGN PATENT DOCUMENTS

DE 102009028666 B3 2/2011
DE 102014221945 A1 4/2016
(Continued)

OTHER PUBLICATIONS

PCT/ISA/210, "International Search Report for International Application No. PCT/JP2017/045334," dated Mar. 6, 2018.
(Continued)

*Primary Examiner* — Elizabeth E Mulvaney
(74) *Attorney, Agent, or Firm* — Manabu Kanesaka (57) ABSTRACT

A ceramic body for dental prosthesis can suppress a variation in quality in the sole ceramic body for dental prosthesis due to expansion of its diameter. The ceramic body for dental prosthesis is made of a ceramic material, is shaped to have a circular planar shape and a disk-like external shape, and has a diameter of 50 mm or more. The method for manufacturing this ceramic body for dental prosthesis includes: preparing a ceramic material; shaping the ceramic material by press shaping or by a machine tool; temporarily sintering the ceramic material at a temperature from a sintering temperature that provides theoretical density −700° C. or more to the sintering temperature −100° C. or less; and shaping the ceramic material to have a circular planar shape and a disk-like external shape so as to prepare the ceramic (Continued)

body for dental prosthesis having a diameter of 50 mm or more.

9 Claims, 2 Drawing Sheets

(51) Int. Cl.
    *A61C 13/083*     (2006.01)
    *C04B 35/64*     (2006.01)
    *G01B 21/20*     (2006.01)
    *G01N 3/40*     (2006.01)
    *G01N 9/00*     (2006.01)
    *G01N 33/38*     (2006.01)

(52) U.S. Cl.
    CPC .............. *C04B 35/64* (2013.01); *G01B 21/20* (2013.01); *G01N 3/40* (2013.01); *G01N 9/00* (2013.01); *G01N 33/388* (2013.01)

(56) References Cited

U.S. PATENT DOCUMENTS

| | | | |
|---|---|---|---|
| 8,141,217 | B2 | 3/2012 | Gubler et al. |
| 9,901,426 | B2* | 2/2018 | Reinshagen ............ C03C 11/00 |
| 2004/0119180 | A1 | 6/2004 | Frank et al. |
| 2008/0199828 | A1 | 8/2008 | Pan et al. |
| 2010/0248936 | A1 | 9/2010 | Yamada et al. |
| 2010/0323327 | A1* | 12/2010 | Eriksson ............ A61C 13/0022 433/199.1 |
| 2012/0114516 | A1* | 5/2012 | Hachenberg .............. B22F 3/11 419/25 |
| 2014/0135200 | A1 | 5/2014 | Reinshagen et al. |
| 2015/0125822 | A1 | 5/2015 | Cramer Von Clausbruch |
| 2017/0020639 | A1* | 1/2017 | Jahns ..................... C04B 35/64 |
| 2018/0055613 | A1* | 3/2018 | Kadobayashi ..... A61C 13/0004 |
| 2018/0221119 | A1* | 8/2018 | Jung ....................... B32B 18/00 |

FOREIGN PATENT DOCUMENTS

| | | |
|---|---|---|
| JP | 2004-527280 A | 9/2004 |
| JP | 2015-511848 A | 4/2015 |
| JP | 5698096 B2 | 4/2015 |

OTHER PUBLICATIONS

PCT/IB/373, "International Preliminary Report on Patentability for International Application No. PCT/JP2017/045334," dated Jul. 30, 2019.

PCT/ISA/237, "Written Opinion of the International Searching Authority for International Application No. PCT/JP2017/045334," dated Mar. 6, 2018.

Europe Patent Office, "Search Report for European Patent Application No. 17894056.5," dated Aug. 19, 2020.

* cited by examiner

METHOD FOR MANUFACTURING CERAMIC SINTERED BODY

RELATED APPLICATIONS

The present application is National Phase of International Application No. PCT/JP2017/045334 filed Dec. 18, 2017, and claims priority from Japanese Application No. 2017-013207, Jan. 27, 2017, the disclosure of which is hereby incorporated by reference herein in its entirety.

TECHNICAL FIELD

The present invention relates to a ceramic body for dental prosthesis and a method for manufacturing the same.

BACKGROUND ART

As a material used for restoring a tooth that is partly lost due to decay or the like, a composite material called as composite resin which is made of an inorganic substance and an organic substance, metal or ceramics are used. In particular, ceramics have not only excellent wear resistance but also excellent appearance, because of enabling to reproduce a color tone close to that of natural teeth, thereby being used as a material for dental prosthesis such as a crown and a bridge.

Conventionally, a dental prosthesis to be attached in a mouth has been structured by coating a surface of a metal frame with ceramics whose color is adjusted into a color tone of natural teeth, but an all-ceramic prosthesis, in which a prosthesis is entirely made of ceramics, has also been getting used. The all-ceramic prosthesis adopts a frame, which is made of, for example, a ceramic sintered body instead of a conventional metal frame, and has an exterior part (that is, a ceramic layer) formed of glass porcelain on a surface of the frame.

The all-ceramic prosthesis has the prosthesis that is entirely formed of ceramics, and thus can suppress or solve various problems including: a problem of a metal allergy that is developed by contacting a living body with metal; and an appearance problem of not obtaining an original color tone of natural teeth due to an opaque underground layer which is provided to hide a metal color.

The dental prosthesis is required to have significantly high dimensional accuracy in the light of occlusion and the like, and thus is produced by a dental CAD/CAM processor. By using such a dental CAD/CAM processor, a shape of the dental prosthesis can be designed on screen using a computer, and a block body made of ceramics can be subjected to cutting processing to have a designed shape of the dental prosthesis by automatic cutting processing, whereby a desired dental prosthesis can be produced. Accordingly, a high-quality dental prosthesis made of ceramics can be produced with high accuracy in a short period of time.

If such manufacturing methods using this dental CAD/CAM processor are roughly divided, following three methods can be exemplified. The first method is a method of performing cutting processing to a ceramic sintered body. The second method is a method including: performing the cutting processing to an unsintered ceramic shaped body; and subsequently performing main sintering on the ceramic shaped body that has been subjected to the cutting processing. The third method is a method including: performing the cutting processing to a temporarily sintered ceramic body; and then performing the main sintering.

The first method is a method of performing the cutting processing to the ceramic sintered body that has been subjected to the main sintering or treated by hot isostatic pressing (HIP) at about 1300° C. to about 1600° C., and does not cause any dimensional change of the ceramic body after the cutting processing. Thus, a dental prosthesis with high dimensional accuracy, which depends on accuracy of a measuring instrument or a processing device of a CAD/CAM processor, can be manufactured. On the other hand, since hardness of the ceramic sintered body is high, a cutting processing time becomes longer, and a tool life of a drill or the like becomes shorter, thereby increasing a manufacturing cost.

The second method is a method including: performing the cutting processing to the ceramic shaped body by considering its shrinkage rate during the main sintering; and subsequently performing the main sintering at 1300° C. to 1600° C. Since a constant shrinkage rate can be obtained according to shaping conditions and density control of the ceramic shaped body, a dental prosthesis with high dimensional accuracy can be manufactured similarly to the above-described first method. On the other hand, strength and hardness of the ceramic shaped body are low, a break, a blemish or the like may be generated during the cutting processing, and since the method includes degreasing processing after the cutting processing, the main sintering requires a time as long as, for example, 10 hours.

In contrast, the third method is a method including: calculating a shrinkage rate during the main sintering from the shrinkage rate during the temporary sintering; performing the cutting processing to the ceramic body by considering the calculated shrinkage rate; and then performing the main sintering at 1300° C. to 1600° C. The temporarily sintered ceramic body has lower hardness than that of the ceramic sintered body which has been subjected to the main sintering, and thus can decrease the cutting processing time, thereby having a merit that the tool life can be longer. Further, since the temporarily sintered ceramic body has higher strength and higher hardness than those of the ceramic shaped body, a break, a blemish or the like during the cutting processing can be suppressed. Moreover, since the degreasing has been completed by the temporary sintering, there also is a merit that a main sintering time after the cutting can be shorter. Accordingly, most of dental prostheses made of ceramics are produced by the third method.

Further, a method including: shaping a temporarily sintered ceramic body so that its planar shape may be circular; providing a convex portion on its entire circumference; and engaging the convex portion with a holding tool of the CAD/CAM processor from an upward/downward direction so as to hold the ceramic body, and the ceramic body are disclosed (for example, see Patent Literature 1).

CITATION LIST

Patent Literature

Patent Literature 1: Japanese Patent No. 5698096

SUMMARY OF INVENTION

Technical Problem

As described above, the appearance and the high dimensional accuracy are required for the ceramic sintered body for dental prosthesis, and high bending strength and compression are sought for satisfying occlusion. However, since the temporarily sintered body described in Patent Literature 1 is a manufactured product in the temporary sintering process, thus is a porous body having many gaps, and further has a diameter larger than 50 mm, a variation in quality is likely to be generated in a sole ceramic body for dental prosthesis due to the enlargement by the expansion of its diameter.

Due to the variation in quality of the ceramic body of the temporarily sintered body, the ceramic sintered body for dental prosthesis after the sintering (main sintering) also has a problem of the appearance such as a variation in color and variations in bending strength and compression.

From the ceramic body for dental prosthesis, fourteenth in a row at maximum can be formed for one dental patient. Thus, since there also is a case of manufacturing a row of teeth for one patient from one ceramic body for dental prosthesis, the variation in quality in the sole ceramic body for dental prosthesis is sought to be suppressed.

The present invention has been made in the light of the above-described problems, and provides a ceramic body for dental prosthesis, which can suppress a variation in quality in the sole ceramic body for dental prosthesis made due to the expansion of its diameter, and can be manufactured easily, and a method for manufacturing the same.

Solution to Problem

The above-described problems can be solved by the following present invention. That is, the ceramic body for dental prosthesis of the present invention is made of a ceramic material, is shaped to have a circular planar shape and a disklike external shape, and has a diameter of 50 mm or more.

Further, the method for manufacturing a ceramic body for dental prosthesis of the present invention includes: preparing a ceramic material; shaping the ceramic material by press shaping or by a machine tool; temporarily sintering the ceramic material is performed at −700° C. or more and −100° C. or less with respect to the sintering temperature that provides theoretical density; and shaping the ceramic material to have a circular planar shape and a disklike external shape so as to prepare a ceramic body for dental prosthesis having a diameter of 50 mm or more.

Advantageous Effects of Invention

According to the ceramic body for dental prosthesis according to the present invention, a variation in quality in the sole ceramic body for dental prosthesis due to expansion of its diameter can be suppressed, and its manufacture can be easier.

DESCRIPTION OF EMBODIMENTS

A first characteristic of the present embodiment is a ceramic body for dental prosthesis, which is made of a ceramic material, is shaped to have a circular planar shape and a disklike external shape, and has a diameter of 50 mm or more.

A second characteristic is a method for manufacturing a ceramic body for dental prosthesis including: preparing a ceramic material; shaping the ceramic material by press shaping or by a machine tool; temporarily sintering the ceramic material is performed at −700° C. or more and −100° C. or less with respect to the sintering temperature that provides theoretical density; and shaping the ceramic material to have a circular planar shape and a disklike external shape so as to prepare the ceramic body for dental prosthesis having a diameter of 50 mm or more.

Incidentally, in the present invention, the disklike external shape denotes an external shape, of which both of one surface and other surface are planes, and which has a desired thickness. Also, the disklike external shape includes an external shape which is provided with a convex portion on its circumference.

Further, in the present invention, the ceramic body for dental prosthesis denotes a solidification body, which has the disklike external shape, is produced by temporary sintering, and is made of ceramics. Moreover, the temporary sintering denotes a process of producing a solidification body (a solidification body made of ceramics) from a ceramic material, and includes half sintering which has been used conventionally, temporary firing and half firing.

A third characteristic is a ceramic body for dental prosthesis, of which a difference between a maximum value and a minimum value of Vickers hardness at plural positions that are away from each other by 45 mm or more on a surface having a planar shape is 15.0 HV or less.

A fourth characteristic is a method for manufacturing a ceramic body for dental prosthesis, including measuring Vickers hardness at plural positions that are away from each other by 45 mm or more on the surface having the planar shape, in which a difference between a maximum value and a minimum value of the Vickers hardness is 15.0 HV or less.

According to these structures or manufacturing methods, the variation in quality in the sole ceramic body for dental prosthesis due to the expansion of its diameter to 50 mm or more can be suppressed. More specifically, the variation in Vickers hardness in the sole ceramic body for dental prosthesis can be suppressed to 15.0 HV or less. Thus, even if, after producing a ceramic sintered body for dental prosthesis from the ceramic body for dental prosthesis, fourteen teeth in a row at maximum are produced as the dental prosthesis from the entire sintered body, the variation in Vickers hardness in each row of the teeth can be suppressed.

Further, since the ceramic body for dental prosthesis can be shaped and produced by shaping the ceramic material by the press shaping or by the machine tool, the manufacture of the ceramic body for dental prosthesis can be easier.

A fifth characteristic is a ceramic body for dental prosthesis, of which a difference between a maximum value and a minimum value of density at plural positions that are away from each other by 45 mm or more on the surface having the planar shape is 0.1 g/cm$^3$ or less.

A sixth characteristic is a method for manufacturing a ceramic body for dental prosthesis, including measuring density at plural positions that are away from each other by 45 mm or more on the surface having the planar shape, in which a difference between a maximum value and a minimum value of the density is 0.1 g/cm$^3$ or less.

According to the structure or the manufacturing method, the variation in density in the sole ceramic body for dental prosthesis due to the expansion of its diameter to 50 mm or more can be suppressed to 0.1 g/cm³ or less. Thus, even if, after producing the ceramic sintered body for dental prosthesis from the ceramic body for dental prosthesis, fourteen teeth in a row at maximum are produced as the dental prosthesis from the entire sintered body, the variation in density in each row of the teeth can be suppressed.

A seventh characteristic is a ceramic body for dental prosthesis, which generates sound having a frequency of 5 kHz or more and 11 kHz or less and a vibration level of −40 dB or more and −20 dB or less, when a center of the surface having the planar shape is tapped.

An eighth characteristic is a method for manufacturing a ceramic body for dental prosthesis, which includes: tapping the center of the surface having the planar shape; and measuring sound having a frequency of 5 kHz or more and 11 kHz or less and a vibration level of −40 dB or more and −20 dB or less.

According to the structure or the manufacturing method, it is possible to quickly check whether a blemish or a crack is present or not in the sole ceramic body for dental prosthesis of 50 mm or more, by the measurement at only one point at the center of the ceramic body. Thus, even if, after producing the ceramic sintered body for dental prosthesis from the ceramic body for dental prosthesis, fourteen teeth in a row at maximum are produced as the dental prosthesis from the entire sintered body, the generation of a blemish or a crack in each row of the teeth can be prevented.

Further, since the measuring point is the only one point at the center of the ceramic body for dental prosthesis, wherever a blemish or a crack is present in the ceramic body for dental prosthesis, the blemish or the crack can be measured from a shortest distance. Thus, since the measurement can be completed only by the one point, and processes can be omitted thereby, the manufacture of the ceramic body for dental prosthesis can be easier.

A ninth characteristic is a ceramic body for dental prosthesis, of which an average ratio of, with respect to external dimensions of sections taken out from at least three positions of the ceramic body for dental prosthesis, external dimensions of the sections after sintering that provide theoretical density is 122% or more and 125% or less.

A tenth characteristic is a method for manufacturing a ceramic body for dental prosthesis including: taking out sections from at least three positions of the ceramic body for dental prosthesis; measuring external dimensions of the taken-out sections; subsequently sintering the sections at a temperature that provides theoretical density; and measuring external dimensions of the sections after main sintering, in which an average ratio of the external dimensions of the sections after the main sintering with respect to the external dimensions of the sections taken out from the ceramic body for dental prosthesis is 122% or more and 125% or less.

According to the structure or the manufacturing method, the average expansion ratio of the sole ceramic body for dental prosthesis from the temporary sintering process and to the completion of the main sintering, which is made due to the expansion of the diameter to 50 mm or more, can be within a range of 122% or more and 125% or less. Thus, even if, after producing the ceramic sintered body for dental prosthesis from the ceramic body for dental prosthesis, fourteen teeth in a row at maximum are produced as the dental prosthesis from the entire sintered body, the variation in expansion ratio of each row of the teeth can be suppressed, whereby a deviation in shape from the time of design can also be suppressed.

An eleventh characteristic is a ceramic body for dental prosthesis, of which a color difference $\Delta E^*ab$ at two positions that are away from each other by 45 mm or more on the surface having the planar shape is 1.0 or less.

A twelfth characteristic is a method for manufacturing a ceramic body for dental prosthesis, including measuring a color difference $\Delta E^*ab$ at two positions that are away from each other by 45 mm or more on the surface having the planar shape, in which the $\Delta E^*ab$ is 1.0 or less.

According to the structure or the manufacturing method, the color difference $\Delta E^*ab$ in the sole ceramic body for dental prosthesis due to the expansion of the diameter to 50 mm or more can be suppressed to 1.0 or less. Thus, even if, after producing the ceramic sintered body for dental prosthesis from the ceramic body for dental prosthesis, fourteen teeth in a row at maximum are produced as the dental prosthesis from the entire sintered body, the variation in color in each row of the teeth can be suppressed, whereby its appearance can be enhanced.

A thirteenth characteristic is a ceramic body for dental prosthesis, of which roundness of the circular planar shape is 1 mm or less.

A fourteenth characteristic is a method for manufacturing a ceramic body for dental prosthesis including measuring roundness of the circular planar shape, in which the roundness is 1 mm or less.

From the above description, the circular planar shape of the ceramic body for dental prosthesis according to the present invention includes not only a planar shape of a perfect circle but also a planar shape with roundness of 1 mm or less.

According to the structure or the manufacturing method, the planar shape of the sole ceramic body for dental prosthesis can be suppressed to the circular shape with the roundness of 1 mm or less. Further, the planar shape of the ceramic body for dental prosthesis is not limited to the perfect circle and can have a certain allowance, whereby the manufacture of the ceramic body for dental prosthesis can be easier.

Hereinafter, a ceramic body for dental prosthesis 1 according to an embodiment of the present invention and a method for manufacturing the same will be described with reference to FIGS. 1, 2A and 2B as appropriate. The ceramic body for dental prosthesis 1 according to the present embodiment is made of a ceramic material, and is shaped to have the disklike external shape as shown in FIG. 1, and further, its planar shape seen from a planar direction is a circular shape as shown in FIG. 2B.

Incidentally, the disklike external shape denotes an external shape of which both of one surface 2a and other surface 2b are planes, and which has a desired thickness T. Further, the disklike external shape includes an external shape which is provided with a convex portion 4 on its circumference.

Figure 1:
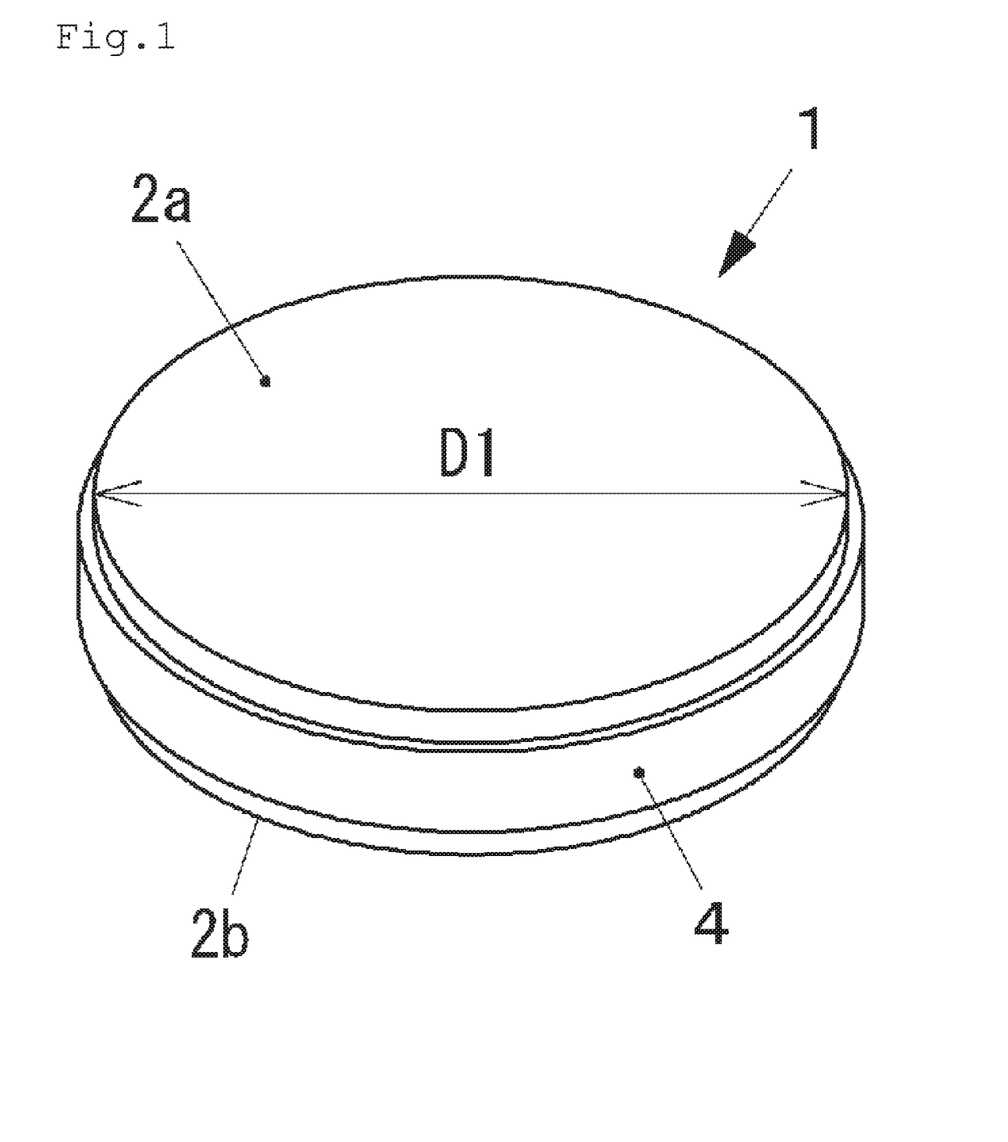
FIG. 1 is a perspective view of a ceramic body for dental prosthesis according to an embodiment of the present invention.
Figure 2A:
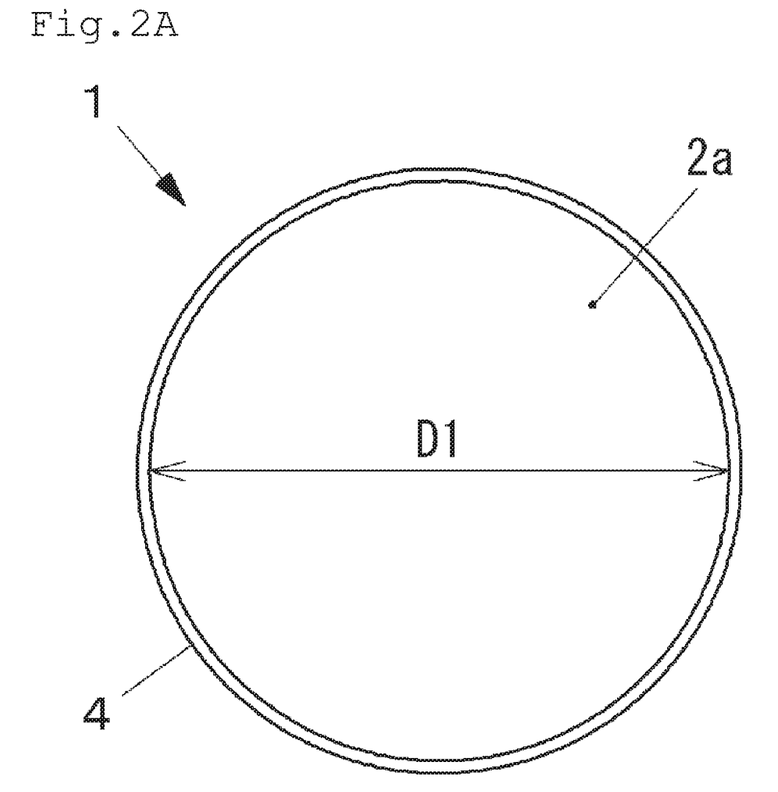
FIG. 2A is a plan view of the ceramic body for dental prosthesis of FIG. 1.
Figure 2B:
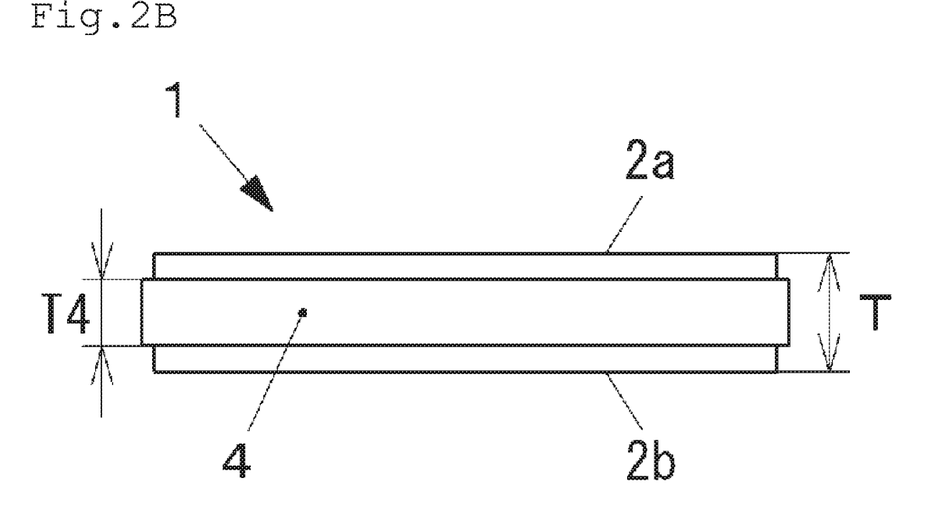
FIG. 2B is a side view of the ceramic body for dental prosthesis of FIG. 1.

The convex portion 4 denotes a part which is formed to protrude convexly along a peripheral direction of the ceramic body for dental prosthesis 1, when the ceramic body for dental prosthesis 1 is seen from its side surface direction, and is formed to at least a part of the periphery of the ceramic body for dental prosthesis 1, as shown in FIGS. 1, 2A, and 2B.

Further, the circular planar shape includes not only a planar shape of a perfect circle but also a planar shape with roundness of 1 mm or less. From the above description, the circular planar shape of the ceramic body for dental prosthesis according to the present invention includes not only the planar shape of the perfect circle but also the planar shape with the measured roundness of 1 mm or less.

Therefore, the planar shape of the sole ceramic body for dental prosthesis 1 can be suppressed to have the circular shape with the roundness of 1 mm or less. Further, the planar shape of the ceramic body for dental prosthesis 1 is not limited to the perfect circle and can have a certain allowance, whereby the manufacture of the ceramic body for dental prosthesis 1 can be easier.

The ceramic body for dental prosthesis 1 is used as a cutting block body for manufacturing a dental prosthesis by cutting processing, and denotes a solidification body made of ceramics, which is produced by temporary sintering. Further, the temporary sintering denotes a process of producing a solidification body (the solidification body made of ceramics) from a ceramic material, and also includes conventionally adopted half sintering, temporary firing or half firing.

The ceramic material for forming the ceramic body for dental prosthesis 1 is any of silica, alumina, zirconia, hydroxyapatite and β-tricalcium phosphate (β-TCP). This ceramic material may be prepared as powder or the like.

Further, a diameter D1 of the one surface 2a and the other surface 2b is preferably 50 mm or more. The reason for this is that 50 mm or more is required to form fourteen human teeth in a row from the ceramic body for dental prosthesis 1.

Incidentally, an upper limit value of the diameter D1 is not limited particularly, but is preferably 110 mm or less, in the light of an acceptable holding range of a holding tool that is provided in a dental CAD/CAM processor.

Moreover, a thickness T of the ceramic body for dental prosthesis 1 can be set arbitrarily, but is preferably 10 mm or more and 30 mm or less, in the light of the acceptable holding range of the holding tool of the dental CAD/CAM processor.

Next, the method for manufacturing the ceramic body for dental prosthesis 1 will be described. Firstly, a ceramic material similarly to that described above is prepared, and is shaped to form a circular planar shape, a disklike external shape and a convex portion 4 similarly to those of the ceramic body for dental prosthesis 1. The shaping is performed by press shaping or by a machine tool. As the machine tool, a milling lathe, a machining center and the like can be exemplified.

Subsequently, the shaped ceramic material is sintered (temporarily sintered) at −700° C. or more and −100° C. or less with respect to the sintering temperature that provides theoretical density, thereby preparing the ceramic body for dental prosthesis 1 made of a porous body that has plural gaps.

Since the ceramic body for dental prosthesis 1 can be shaped to be produced by shaping the ceramic material by the press shaping or by the machine tool, the manufacture of the ceramic body for dental prosthesis 1 can be easier.

Incidentally, the sintering temperature that provides the theoretical density denotes a sintering temperature (a main sintering temperature) at which a ceramic sintered body produced from a desired ceramic material can obtain theoretical density. More specifically, the sintering temperature denotes a sintering temperature, at which a ceramic sintered body is formed, for providing respective theoretical density of 2.20 g/cm³ of silica, 3.99 g/cm³ of alumina, 6.07 g/cm³ of zirconia, 3.16 g/cm³ of hydroxyapatite and 3.07 g/cm³ of β-TCP. The temporary sintering is performed at −700° C. or more and −100° C. or less with respect to the sintering temperature.

An example of the sintering temperature (the main sintering temperature) of each ceramic sintered body that provides the theoretical density is as follows: 1400° C. of silica; 1550° C. of alumina; 1450° C. of zirconia; 1300° C. of hydroxyapatite; and 1300° C. of β-TCP.

The temporary sintering temperature of the porous ceramic body for dental prosthesis 1 depends on a kind or a particle size of the ceramic material, but is preferably not more than a temperature, at which pores of the porous body are not closed even when the temporary sintering proceeds, and the temporary sintering is preferably performed at 850° C. or more and 1050° C. or less as its specific numerical range. An atmosphere for performing the temporary sintering may be air or a non-oxidizing atmosphere such as nitrogen, rare gas including argon and the like.

As a method for producing the porous body, powder of the ceramic material may be shaped and subjected to the temporary sintering as described above, or the powder of the ceramic material, to which an organic binder or an inorganic binder is added, may be shaped and subjected to the temporary sintering.

Next, a variation in Vickers hardness, a variation in density, a tap tone vibration level, an average expansion ratio and a color difference ΔE*ab of the prepared ceramic body for dental prosthesis 1 are measured so as to perform inspection for screening between non-defective products and defective products.

The measurement of Vickers hardness is adopts a Vickers tester, and is performed by pushing an indenter of the Vickers tester against the surface having the planar shape of the prepared ceramic body for dental prosthesis 1. The indenter is pushed against either of the one surface 2a and the other surface 2b at plural positions (at least two positions) that are away from each other by 45 mm or more.

Pushing force of the indenter is 0.3 kgf (about 2.94 N), and a retention time thereof is 10 seconds, so that impressions are formed on either of the one surface 2a and the other surface 2b of the ceramic body for dental prosthesis 1. The Vickers hardness is measured plural times at the plural positions, thereby deriving a difference between a maximum value and a minimum value thereof.

In the present invention, a ceramic body for dental prosthesis is determined as a non-defective product, if the difference between the maximum value and the minimum value of the Vickers hardness at the plural positions in the sole ceramic body for dental prosthesis 1 is 15.0 HV or less, and a ceramic body for dental prosthesis is determined as a defective product, if the difference is more than 15.0 HV.

The present applicant has confirmed that the variation in Vickers hardness is one of the factors that affect variations in bending strength and compression which determines occlusion of rows of teeth for dental prosthesis, by verification. If a row of teeth for dental prosthesis is produced by performing the main sintering on the sole ceramic body for dental prosthesis having the variation in Vickers hardness of more than 15.0 HV, the variation in Vickers hardness of more than 15.0 HV is generated also in each row of the teeth, whereby occlusion may be affected.

Further, the reason for separating the measurement positions of the Vickers hardness by at least 45 mm is that, if the measurement positions are separated by 50 mm in the ceramic body for dental prosthesis having the diameter D1 of 50 mm, one of the measurement positions comes to an edge of the surface having the planar shape, so that the indenter measurement becomes difficult. Thus, in the light of performing the quality measurement at the measurement positions that are away from each other while securing a margin for the measurement, due to the setting of the separating distance between the measurement positions to be at least 45 mm and the setting of the diameter D1 to be 50 mm or more, the separating distance between the measurement positions is also set to be 45 mm or more.

According to these structures, the variation in quality in the sole ceramic body for dental prosthesis 1 due to the expansion of the diameter to 50 mm or more can be suppressed. More specifically, the variation in Vickers hardness in the sole ceramic body for dental prosthesis 1 can be suppressed to 15.0 HV or less. Thus, even if, after producing the ceramic sintered body for dental prosthesis from the ceramic body for dental prosthesis 1, fourteen teeth in a row at maximum are produced as the dental prosthesis from the entire sintered body, the variation in Vickers hardness in each row of the teeth can be suppressed.

Next, the measurement of a variation in density adopts an electronic balance. Sections are taken out from at least two positions that are away from each other by 45 mm or more on either of the one surface 2a and the other surface 2b of the prepared ceramic body for dental prosthesis 1, weight of the respective taken-out sections in an atmosphere and in water is measured by an Archimedes method, thereby obtaining weight differences. Further, from the weight differences, density at the plural positions (at least the two positions) that are away from each other by 45 mm or more on either of the one surface 2a and the other surface 2b is calculated. A water temperature during the underwater measurement can be set at, for example, 21° C. to 22° C.

Then, the density is measured plural times at the plural positions (at least the two positions) that are away from each other by 45 mm or more, and a difference between a maximum value and a minimum value is derived.

In the present invention, a ceramic body for dental prosthesis is determined as a non-defective product, if the difference between the maximum value and the minimum value of the density at the plural positions in the sole ceramic body for dental prosthesis 1 is 0.1 g/cm3 or less, and a ceramic body for dental prosthesis is determined as a defective product, if the difference is more than 0.1 g/cm3.

The present applicant has confirmed that the variation in density is one of the factors that affect the variations in bending strength and compression which determines occlusion of rows of teeth for dental prosthesis, by their verification. If a row of teeth for dental prosthesis is produced by performing the main sintering on the sole ceramic body for dental prosthesis having the variation in density of more than 0.1 g/cm$^3$, the variation of more than 0.1 g/cm$^3$ is generated also in each row of the teeth, whereby occlusion may be affected.

Further, the reason for separating the measurement positions of the density by at least 45 mm is that, if the measurement positions are separated by 50 mm in the ceramic body for dental prosthesis having the diameter D1 of 50 mm, one of the measurement positions comes to an edge of the surface having the planar shape, so that the measurement becomes difficult. Thus, in the light of performing the quality measurement at the measurement positions that are away from each other while securing a margin for the measurement, due to the setting of the separating distance between the measurement positions to be at least 45 mm and the setting of the diameter D1 to be 50 mm or more, the separating distance between the measurement positions is also set to be 45 mm or more.

According to these structures, the variation in density in the sole ceramic body for dental prosthesis 1 due to the expansion of the diameter to 50 mm or more can be suppressed to 0.1 g/cm$^3$ or less. Thus, even if, after producing the ceramic sintered body for dental prosthesis from the ceramic body for dental prosthesis 1, fourteen teeth in a row at maximum are produced as the dental prosthesis from the entire sintered body, the variation in density in each row of the teeth can be suppressed.

Next, the measurement of the tap tone vibration level is performed while the prepared ceramic body for dental prosthesis 1 is placed, for example, on a cushioning material used for packaging, and further a microphone is disposed in a space above a plane (for example, the one surface 2a in the case of FIG. 1) that is an upper surface. The microphone is disposed at a central position of the one surface 2a in the space that is away from the plane of the one surface 2a in a height direction (that is, a thickness T direction) by 10 mm.

Next, the center of the surface (the center of the one surface 2a) of the planar shape of the ceramic body for dental prosthesis 1 is tapped with a stick so as to generate sound. The stick is made of fluororesin for preventing damage of the ceramic body for dental prosthesis 1 at the time of tapping by the stick, a diameter of the stick is set to be 5 mm to 10 mm, and force to drop down the stick at the time of tapping is set to be 0.025 N to 0.03 N.

In the present invention, sound generated at the time when the prepared ceramic body for dental prosthesis 1 is tapped is collected by the microphone, and a vibration level (dB) of the collected sound is measured. Then, a ceramic body for dental prosthesis which generates sound of −40 dB or more and −20 dB or less in a range of a frequency of 5 kHz or more and 11 kHz or less is determined as a non-defective product, and a ceramic body for dental prosthesis which generates sound of less than −40 dB or more than −20 dB is determined as a defective product.

The present applicant has found that the vibration level (dB) of the sound generated by the tapping sound measurement can be used for determination of presence or absence of a blemish or a crack in a row of teeth for dental prosthesis, by verification. The presence or absence of a blemish or a crack affects the variations in bending strength and compression which determines occlusion. The present applicant has found, according to their verification, if the vibration level (dB) of the collected sound is less than −40 dB or more than −20 dB in the range of the frequency of 5 kHz or more and 11 kHz or less, a blemish or a crack is present in the ceramic body for dental prosthesis 1. It has been found that, if the sole ceramic body for dental prosthesis 1 is subjected to the main sintering so as to produce a row of teeth for dental prosthesis, the variations in bending strength and compression are generated in each row of the teeth depending on the number or a size of the blemish(es) or the crack(s), whereby occlusion may be affected.

According to the above-described structure, it is possible to quickly measure whether a blemish or a crack is present or not in the sole ceramic body for dental prosthesis 1 of 50 mm or more, by the measurement at only one point at the center of the ceramic body 1. Thus, even if, after producing the ceramic sintered body for dental prosthesis from the ceramic body for dental prosthesis 1, fourteen teeth in a row at maximum are produced as the dental prosthesis from the entire sintered body, the generation of a blemish or a crack in each row of the teeth can be prevented.

Further, since the measuring point is the only one point at the center of the ceramic body 1, wherever a blemish or a crack is present in the ceramic body for dental prosthesis 1, the blemish or the crack can be measured from a shortest distance. Thus, since the measurement can be completed by the only one point, and processes can be omitted thereby, the manufacture of the ceramic body for dental prosthesis 1 can be easier.

Next, measurement of the average expansion ratio (%) is performed by: taking out sections from at least three arbitrary points of the prepared ceramic body for dental prosthesis 1; measuring external dimensions of the taken-out sections; sintering (main sintering) the sections at a temperature that provides theoretical density; measuring external dimensions of the sections after the main sintering; and dividing the external dimension of the taken-out section by the external dimension of the section after the main sintering.

As the positions for taking out the sections, a central position of the ceramic body for dental prosthesis 1, a position near an outer periphery thereof, and a middle position between the central position and the position near the outer periphery can be exemplified for cutting out in a form of cubes.

The expansion ratios of the prepared ceramic body for dental prosthesis 1 is derived by: measuring respective vertical, horizontal and height dimensions of the cut-out cube in three dimensional directions as the external dimensions; performing main sintering on the cube; measuring respective vertical, horizontal and height dimensions of the cube after the main sintering in three dimensional directions; calculating quotients of the dimensions in the respective directions. Thus, the average expansion ratio (%) is represented by (the vertical, horizontal and height dimensions of the taken-out section)/(the vertical, horizontal and height dimensions of the section after the main sintering), which are average ratios in the respective three dimensional directions.

The main sintering of the section may be performed according to the ceramic material of the prepared ceramic body for dental prosthesis 1 at the sintering temperature of each ceramic sintered body that provides the theoretical density (the main sintering temperature).

In the present invention, a ceramic body for dental prosthesis is determined as a non-defective product, if its average expansion ratio of respective dimensions in the three dimensional directions of the sections that are taken out from at least three positions is 122% or more and 125% or less, and a ceramic body for dental prosthesis having an average expansion ratio of less than 122% or more than 125% is determined as a defective product.

The present applicant has confirmed that the variation in average expansion ratio is one of the factors that affect the variations in bending strength and compression which determines occlusion of rows of teeth for dental prosthesis, by verification. If a row of teeth for dental prosthesis is produced by performing the main sintering on the sole ceramic body for dental prosthesis having the average expansion ratio of less than 122% or more than 125%, the row of the teeth having the average expansion ratio of less than 122% or more than 125% is generated, the variations in bending strength and compression are generated, and a deviation in shape from the time of design is increased, whereby occlusion may be affected.

Further, the present applicant has found that the reason for measuring the expansion ratios at least three positions is that, since the ceramic body for dental prosthesis 1 is a porous body, the measurement of the sections at least three positions is required for measuring the variation in average expansion ratio, by verification. For measuring the expansion ratios at, for example, two measuring positions so as to measure the average expansion ratio of the ceramic body for dental prosthesis 1 having the diameter D1 of 50 mm or more, a form of taking out the sections both near the outer periphery as the positions that are most away from each other can be considered. The applicant of the present invention has been found that, in this case, if calculating the average expansion ratio, a ceramic body for dental prosthesis having the average expansion ratio of less than 122% or more than 125% is likely to emerge, and a non-defective product may be determined as a defective product, by verification.

Incidentally, in the case of the comparatively thick ceramic body for dental prosthesis 1, the sections may be taken out at totally six positions, which are two positions along the thickness T direction at each of: a central position; a position near the outer periphery; and a middle position between the central position and the position near the outer periphery of the ceramic body for dental prosthesis 1.

According to these structures, the average expansion ratio of the sole ceramic body for dental prosthesis 1 from the temporary sintering process and to the completion of the main sintering, which is due to the expansion of its diameter to 50 mm or more, can be within the range of 122% or more and 125% or less. Thus, even if, after producing the ceramic sintered body for dental prosthesis from the ceramic body for dental prosthesis 1, fourteen teeth in a row at maximum are produced as the dental prosthesis from the entire sintered body, the variation in expansion ratio of each row of the teeth can be suppressed, whereby the variation in shape from the time of design can also be suppressed.

Next, the measurement of the color difference $\Delta E^*ab$ is performed using a colorimeter or a color meter by: measuring colors by $L^*a^*b$ on the surface having the planar shape of the prepared ceramic body for dental prosthesis 1 respectively at two positions that are away from each other by 45 mm or more on either of the one surface 2a and the other surface 2b; and obtaining the color difference $\Delta E^*ab$ from a difference of distances L of the two positions by a following Formula 1 of a color difference $\Delta E^*ab$ formula. As an example of the measurement positions, a central position of the ceramic body for dental prosthesis 1, a position near an outer periphery thereof which is away from another measurement position by 45 mm or more, and the like can be exemplified.

$$\Delta E^*ab = \sqrt{(\Delta L^*)^2 + (\Delta a^*)^2 + (\Delta b^*)^2} \qquad \text{[Formula 1]}$$

In the present invention, a ceramic body for dental prosthesis is determined as a non-defective product, if the color difference $\Delta E^*ab$ at the two positions in the sole ceramic body for dental prosthesis 1 is 1.0 or less, and a ceramic body for dental prosthesis having the color difference $\Delta E^*ab$ of more than 1.0 is determined as a defective product.

The present applicant has found that, if a row of teeth for dental prosthesis is produced by performing the main sintering on the sole ceramic body for dental prosthesis that has the color difference $\Delta E^*ab$ of more than 1.0, a variation in color which can be discriminated by visual observation is generated in each row of the teeth, and its appearance is lost, by verification.

Further, the reason for separating the measurement positions of the color difference $\Delta E^*ab$ by at least 45 mm is that, if the measurement positions are separated by 50 mm in the ceramic body for dental prosthesis having the diameter D1 of 50 mm, one of the measurement positions comes to an edge of the surface having the planar shape, so that the color measurement by $L^*a^*b$ becomes difficult. Thus, in the light of performing the quality measurement at the measurement positions that are away from each other while securing a margin for the measurement, due to the setting of the separating distance between the measurement positions to be at least 45 mm and the setting of the diameter D1 to be 50 mm or more, the separating distance between the measurement positions is also set to be 45 mm or more.

According to these structures, the color difference ΔE*ab in the sole ceramic body for dental prosthesis 1 due to the expansion of the diameter to 50 mm or more can be suppressed to 1.0 or less. Thus, even if, after producing the ceramic sintered body for dental prosthesis from the ceramic body for dental prosthesis 1, fourteen teeth in a row at maximum are produced as the dental prosthesis from the entire sintered body, the variation in color in each row of the teeth can be suppressed, whereby the appearance can be enhanced.

As described above, in the ceramic body for dental prosthesis according to the present invention and the method for manufacturing the same, it has been found that the Vickers hardness, the variation in density, the tap tone vibration level and the average expansion ratio can be exemplified as the factors that affect the bending strength and the compression which are important for the dental prosthesis purpose, and the appearance according to the color difference ΔE*ab is also considered.

Further, the present applicant has derived the extents to which the variations and the numeric values of the respective measuring objects exemplified as the factors are suppressed or set, for causing no problem in the points of the bending strength and the compression which are important for the dental prosthesis purpose or in the point of the appearance, and for enabling the variation in quality in the sole ceramic body for dental prosthesis to be suppressed, by verification.

Moreover, also by deriving the extents to which the measurement positions and the number of the measurements, which are required for each of the measuring objects exemplified as the factors, cab be decreased, the screening inspection process for discriminating between the non-defective products and the defective products can be simplified, and the manufacture of the ceramic body for dental prosthesis can be easier.

From the above description, even in a case of the ceramic body for dental prosthesis having the diameter expanded to 50 mm or more, an yield of the ceramic body for dental prosthesis can be improved, whereby mass production can be improved.

REFERENCE SIGNS LIST 1 ceramic body for dental prosthesis
2a one surface
2b other surface
4 convex portion
D1 diameter
T thickness of ceramic body for dental prosthesis
T4 thickness of convex portion

The invention claimed is:

1. A method for manufacturing a ceramic sintered body for dental prosthesis from a ceramic body for dental prosthesis, the method comprising:
preparing a ceramic material;
shaping the ceramic material having a sole ceramic body by press shaping or by a machine tool to have a circular planar shape and a disklike external shape so as to prepare the sole ceramic body for dental prosthesis having a diameter of 50 mm or more and 110 mm or less and a thickness of 10 mm or more and 30 mm or less;
temporarily sintering the ceramic material performed at 850° C. or more and 1050° C. or less so that pores of a porous body of the ceramic material are not closed even when the temporary sintering proceeds;
measuring Vickers hardness at plural positions of the sole ceramic body for dental prosthesis that are away from each other by 45 mm or more on a surface having the planar shape, wherein a difference between a maximum value and a minimum value of the Vickers hardness is 15.0 HV or less; and
producing the ceramic sintered body for dental prosthesis from the ceramic body by subjecting the ceramic body for dental prosthesis to a main sintering at temperatures that provides theoretical density so as to produce a row of teeth for dental prosthesis.

2. The method according to claim 1, further comprising measuring density of the ceramic body for dental prosthesis at plural positions that are away from each other by 45 mm or more on a surface having the planar shape, wherein a difference between a maximum value and a minimum value of the density is 0.1 g/cm$^3$ or less.

3. The method according to claim 1, further comprising: tapping a center of a surface of the ceramic body for dental prosthesis having the planar shape; and measuring sound having a frequency of 5 kHz or more and 11 kHz or less and a vibration level of −40 dB or more and −20 dB or less.

4. The method according to claim 1, further comprising: taking out sections from at least three positions of the ceramic body for dental prosthesis; measuring outer diameter dimensions of the taken-out sections; subsequently sintering the sections at a temperature that provides theoretical density; and measuring external dimensions after main sintering, wherein an average ratio of the external dimensions of the sections after the main sintering, with respect to the external dimensions of the sections taken out from the ceramic body for dental prosthesis, is 122% or more and 125% or less.

5. The method according to claim 1, further comprising measuring a color difference ΔE*ab at two positions of the ceramic body for dental prosthesis that are away from each other by 45 mm or more on a surface having the planar shape, wherein the ΔE*ab is 1.0 or less.

6. The method according to claim 1, further comprising measuring roundness of the circular planar shape of the ceramic body for dental prosthesis, wherein the roundness is 1 mm or less.

7. The method according to claim 1, wherein after shaping the ceramic material to have the circular planar shape and the disklike external shape, a variation in density, a tap tone vibration level, an average expansion ratio and a color difference ΔE*abv of the prepared ceramic body for dental prosthesis are measured so as to perform inspection for screening between non-defective products and defective products.

8. The method according to claim 1, wherein the temporary sintering is performed at a non-oxidizing atmosphere.

9. The method according to claim 1, wherein in preparing the ceramic material, powder of the ceramic material is mixed with an organic binder or an inorganic binder.

* * * * *